United States Patent
Froggatt et al.

(10) Patent No.: US 11,324,393 B2
(45) Date of Patent: May 10, 2022

(54) AUGMENTED ACCURACY USING LARGE DIAMETER SHAPE FIBER

(71) Applicant: INTUITIVE SURGICAL OPERATIONS, INC., Sunnyvale, CA (US)

(72) Inventors: Mark E. Froggatt, Blacksburg, VA (US); Eric Sanborn, Blacksburg, VA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 458 days.

(21) Appl. No.: 16/325,273

(22) PCT Filed: Aug. 15, 2017

(86) PCT No.: PCT/US2017/046941
§ 371 (c)(1),
(2) Date: Feb. 13, 2019

(87) PCT Pub. No.: WO2018/035122
PCT Pub. Date: Feb. 22, 2018

(65) Prior Publication Data
US 2019/0183318 A1    Jun. 20, 2019

Related U.S. Application Data

(60) Provisional application No. 62/375,787, filed on Aug. 16, 2016.

(51) Int. Cl.
*A61B 1/00* (2006.01)
*A61B 1/005* (2006.01)
(Continued)

(52) U.S. Cl.
CPC .......... *A61B 1/00167* (2013.01); *A61B 1/005* (2013.01); *A61B 1/04* (2013.01);
(Continued)

(58) Field of Classification Search
CPC ... A61B 1/00167; A61B 5/6852; A61B 1/005; A61B 2090/3614; A61B 2034/2061; A61B 1/00154; A61M 25/01
See application file for complete search history.

(56) References Cited

U.S. PATENT DOCUMENTS 7,720,322 B2    5/2010    Prisco
7,781,724 B2    8/2010    Childers et al.
(Continued)

FOREIGN PATENT DOCUMENTS

CN    1241397 A    1/2000
CN    101884524 A    11/2010
(Continued)

OTHER PUBLICATIONS

Extended European Search Report for Application No. EP17841992.5, dated Mar. 23, 2020, 8 pages.
(Continued)

*Primary Examiner* — Ashley K Buran
*Assistant Examiner* — Delia M. Appiah Mensah
(74) *Attorney, Agent, or Firm* — Schwegman Lundberg & Woessner, P.A.

(57) ABSTRACT

Where a flexible tool includes a tool body with a flexible portion, a distal end and a first optical fiber within the flexible portion, shape sensing can be achieved with increased accuracy by inserting or otherwise including a second optical fiber within the flexible portion. The increased accuracy can be achieved when the second optical fiber has a diameter larger than that of the first optical fiber. Once the shape of the flexible tool has been determined using at least the second optical fiber, the first optical fiber can be used for subsequent shape sensing. This may be particularly applicable where the tool includes an instrument such as an optical imaging device inserted in a channel of the
(Continued)

tool, where not all of the width of the channel is occupied by functional components behind the operable end of the instrument.

10 Claims, 2 Drawing Sheets

(51) Int. Cl.
*A61B 5/06* (2006.01)
*A61M 25/01* (2006.01)
*A61B 5/00* (2006.01)
*A61B 34/20* (2016.01)
*A61B 1/04* (2006.01)
*A61B 5/08* (2006.01)
*A61B 90/00* (2016.01)

(52) U.S. Cl.
CPC ............... *A61B 5/06* (2013.01); *A61B 5/065* (2013.01); *A61B 5/6852* (2013.01); *A61B 34/20* (2016.02); *A61M 25/01* (2013.01); *A61B 5/08* (2013.01); *A61B 2034/2061* (2016.02); *A61B 2090/3614* (2016.02); *A61B 2560/0266* (2013.01)

(56) References Cited

U.S. PATENT DOCUMENTS

| | | | |
|---|---|---|---|
| 8,460,236 | B2 | 6/2013 | Roelle et al. |
| 8,567,265 | B2 | 10/2013 | Aeby et al. |
| 8,672,837 | B2 | 3/2014 | Roelle et al. |
| 2013/0030363 | A1 | 1/2013 | Wong et al. |
| 2013/0204124 | A1 | 8/2013 | Duindam et al. |
| 2013/0310645 | A1 | 11/2013 | Desjardins et al. |
| 2014/0066756 | A1* | 3/2014 | Sinclair .................. G02B 6/322 600/427 |
| 2015/0190123 | A1* | 7/2015 | Park ................... A61B 10/0266 600/567 |
| 2016/0081761 | A1 | 3/2016 | Kuboi et al. |

FOREIGN PATENT DOCUMENTS

| | | |
|---|---|---|
| EP | 2006892 A1 | 12/2008 |
| EP | 2979612 A1 | 2/2016 |
| EP | 3006892 AI | 4/2016 |
| JP | 2011-200341 | 10/2011 |
| WO | WO-2012101532 A1 | 12/2008 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Written Opinion for Application No. PCT/US2017/046941, dated Nov. 28, 2017, 7 pages.

International Preliminary Report on Patentability for Application No. PCT/US2017/046941, dated Feb. 28, 2019, 9 pages.

International Search Report for PCT/US2017/046941 dated Nov. 28, 2017, 2 pages.

* cited by examiner

AUGMENTED ACCURACY USING LARGE DIAMETER SHAPE FIBER

This application is the U.S. national phase of International Application No. PCT/US2017/046941 filed Aug. 15, 2017 which designated the U.S. and claims priority to U.S. Provisional Patent Application 62/375,787, filed Aug. 16, 2016, entitled "AUGMENTED ACCURACY USING LARGE DIAMETER SHA PE FIBER." the entire contents of each of which are hereby incorporated by reference.

BACKGROUND

Various techniques for an optical fiber and application thereof are known.

For example, the following patents all discuss aspects of detecting the shape of an optical fiber, or the application of such detection: U.S. Pat. Nos. 7,781,724, 7,720,322, 8,460,236, 8,672,837, 8,567,265, all of which are hereby incorporated by reference in their entireties.

BRIEF SUMMARY

One application of optical fibers that sense the shape of a flexible tool is to use shape sensing to aid in navigating a catheter through a passage in a mammalian body (e.g., through a human lung). The optical fiber used to sense shape in the catheter (an example of a flexible tool) may be embedded into the wall of the catheter so that the optical fiber does not interfere with an instrument that is inserted into the catheter. In an embodiment, the optical fiber in the wall has diameter (or cross-sectional area) that is minimized to leave a relatively large central working channel in the catheter. For this embodiment, for most of the navigation to the site of interest in the lung, an optical imaging device (e.g., a camera or a portion thereof such as lens that can collect light for image processing) is in this relatively large central channel. Since a large channel is desirable for allowing the largest possible tools and/or optical imaging devices into the catheter, and a small overall catheter diameter is desirable to allow navigation in the smallest possible bronchiole, it is preferable to minimize the thickness of the wall of the catheter. Consequently, the shape sensing fiber has a diameter or thickness that is as small as possible for a particular set of design and operation constraints. Smaller fiber diameters reduces the accuracy of the shape sensor versus the accuracy that could be achieved if the diameter of the shape sensing fiber was larger, such as in cases where the fiber diameter is not limited by thickness of the wall of the catheter. This reduction in accuracy follows the square of the ratio of the diameters (or radius) of the fiber. If the total diameter of the optical fiber is increased from 200 microns to 500 microns, then the accuracy of the position sensing could be expected to improve by a factor of about 5 or 6. But the larger diameter fiber may be too large to fit in the wall of some catheter designs. Larger diameter fibers in the wall of a catheter also generally reduces the size of the central working channel, and the amount of usable space in the central working channel in the catheter.

When the catheter is initially inserted in anatomy, in some examples it can be preferable to provide an instrument with an optical imaging device through the working channel of the catheter such that the optical imaging device is available at a catheter distal end. In this way the operator can be provided with an image to assist with navigating the catheter. The optical imaging device may be sized to occupy substantially all of the diameter (or width) of the working channel, but the control lines (e.g., electrical wires) for the optical imaging device may require less space than the optical imaging device. Thus the space behind the optical imaging device (where the control lines are located) is largely wasted during the insertion process.

An aspect of the present technology solves one or more problems of the prior art.

An aspect of the present technology includes a flexible tool comprising: a tool body with a flexible portion, a proximal end and a distal end; a first optical fiber within the flexible portion, the first optical fiber having a first diameter; and a second optical fiber configured to be inserted within the flexible portion, the second optical fiber having a second diameter, the second diameter being larger than the first diameter; wherein the first optical fiber and the second optical fiber are each configured to sense a shape of the flexible portion of the tool body.

Embodiments may further include none, a combination of, or all of the following. In examples, (a) the tool body further comprises a channel and the second optical fiber is configured to be inserted within the channel; (b) the flexible tool further comprises an instrument configured to be inserted within the channel, where the instrument includes an operation line and an operable component, where the operable component having a larger major dimension normal (orthogonal) to a longitudinal axis of the channel than the operation line, and where the second optical fiber is attached to the operable component; (c) the instrument is removable from the channel; (d) the operable component is an optical imaging device; (e) the flexible tool further comprises an instrument configured to be inserted within the channel, where the instrument includes an operation line and an operable component, where the operable component has a larger major dimension normal (orthogonal) to a longitudinal axis of the channel than the operation line, wherein the second optical fiber is configured to be inserted in the channel to adjacent the operation line; (f) the channel is within the flexible portion; (g) the channel is coextensive with the flexible portion; (h) the first optical fiber is fixed to a wall of the tool body; (i) the first optical fiber is within a wall of the tool body; (j) the system further comprises a control system. The control system may be configured to: (a) sense the shape of the flexible tool using at least the second optical fiber after the second optical fiber has been inserted into the flexible portion, and sense the shape of the flexible tool using the first optical fiber and not the second optical fiber after the second optical fiber has been removed from the flexible portion; (b) determine whether the second optical fiber is inserted into the flexible tool (such as the channel, the flexible portion etc.); (c) determine a correction for the first optical fiber based on a reading from the second optical fiber; and/or (d) sense the shape of the flexible tool using the first optical fiber by: using a reading from the first optical fiber and the correction. The correction may be used to adjust the reading from the first optical fiber, the resulting shape calculations based on the first optical fiber, or any intermediate calculations or parameters.

An aspect of the present technology includes a flexible tool comprising: a tool body with a flexible portion, a proximal end and a distal end; a first optical fiber within the flexible portion, the first optical fiber having a first end fixed to the tool body near the distal end and having a first diameter; a second optical fiber configured to be inserted within the flexible portion, the second optical fiber having a second end near the distal end and having a second diameter that is larger than the first diameter, the second optical fiber being repeatably insertable and removable from the tool body; wherein the first optical fiber and the second optical fiber are each configured to sense a shape of the flexible portion.

Embodiments may further include none, a combination of, or all of the following. In examples, (a) the tool body comprises a channel and the second optical fiber is configured to be inserted within the channel; (b) the first optical fiber is fixed to a wall of the tool body; (c) the first optical fiber is within a wall of the tool body; (d) the channel is within the flexible portion; (e) the channel is coextensive with the flexible portion; (f) the flexible tool further comprises an instrument configured to be inserted within the tool body, where the instrument is repeatably insertable and removable, and where the second optical fiber is attached to the instrument; and/or (g) the instrument comprises an optical imaging device.

An aspect of the present technology includes a method for improving accuracy of shape sensing of a flexible tool with a first optical fiber configured to sense a shape of the flexible tool, the method comprising: inserting a second optical fiber into a channel of the flexible tool wherein the second optical fiber includes a diameter larger than that of the first optical fiber; sensing a shape of the flexible tool using at least the second optical fiber; removing the second optical fiber from the tool; and sensing the shape of the flexible tool using only the first optical fiber after the second optical fiber has been removed.

Embodiments may further include none, a combination of, or all of the following. In examples, (a) the method further comprises: inserting an operable element into the tool after the second optical fiber is removed; and performing an action with the operable element simultaneous to the sensing the shape of the flexible tool using only the first optical fiber, and/or (b) the method further comprises: changing the shape of the flexible tool; and re-sensing the shape of the flexible tool using at least the second optical fiber.

An aspect of the present technology includes a method for sensing a shape of the flexible tool comprising: sensing the shape of the flexible tool using at least a second optical fiber after the second optical fiber has been inserted into a channel of the flexible tool; and sensing the shape of the flexible tool using the first optical fiber and not the second optical fiber after the second optical fiber has been removed from the channel. The second optical fiber includes a diameter larger than that of the first optical fiber.

Embodiments may further include none, a combination of, or all of the following. In examples, the method further comprises: (a) performing an action with an operable element simultaneous to the sensing the shape of the flexible tool using the first optical fiber after the second optical fiber has been removed and the operable element has been inserted into the flexible tool; (b) determining that the second optical fiber has been inserted into the channel; (c) determining that the second optical fiber has been removed from the channel; (d) sensing the shape of the flexible tool using only the first optical fiber; (e) determining a correction for the first optical fiber based on a reading from the second optical fiber; (f) sensing the shape of the flexible tool using the first optical fiber comprises: using a reading from the first optical fiber and the correction.

One or more of the aspects and examples above may be advantageous because an optical fiber in the channel of the flexible tool may share space with an instrument in the channel (e.g., share space with the cabling of a camera, biopsy needle, etc.). More accurate measurements may be obtained because the fiber in the channel may be larger and thus more accurate, and/or the fiber could be used to correct errors in measurements from a smaller fiber in the wall of the flexible tool. When the instrument is removed, the catheter is generally not moved substantially, and the smaller fiber could perform a more accurate differential measurement of the changes in the tool once the instrument is removed. Thus benefits of the fiber in the channel can be realized even after its removal.

Other aspects, features, and advantages of this technology will become apparent from the following detailed description when taken in conjunction with the accompanying drawings, which are a part of this disclosure and which illustrate, by way of example, principles of this technology.

DETAILED DESCRIPTION

The following description is provided in relation to several examples which may share common characteristics and features. It is to be understood that one or more features of any one example may be combinable with one or more features of the other examples. In addition, any single feature or combination of features in any of the examples may constitute additional examples.

Figure 1:
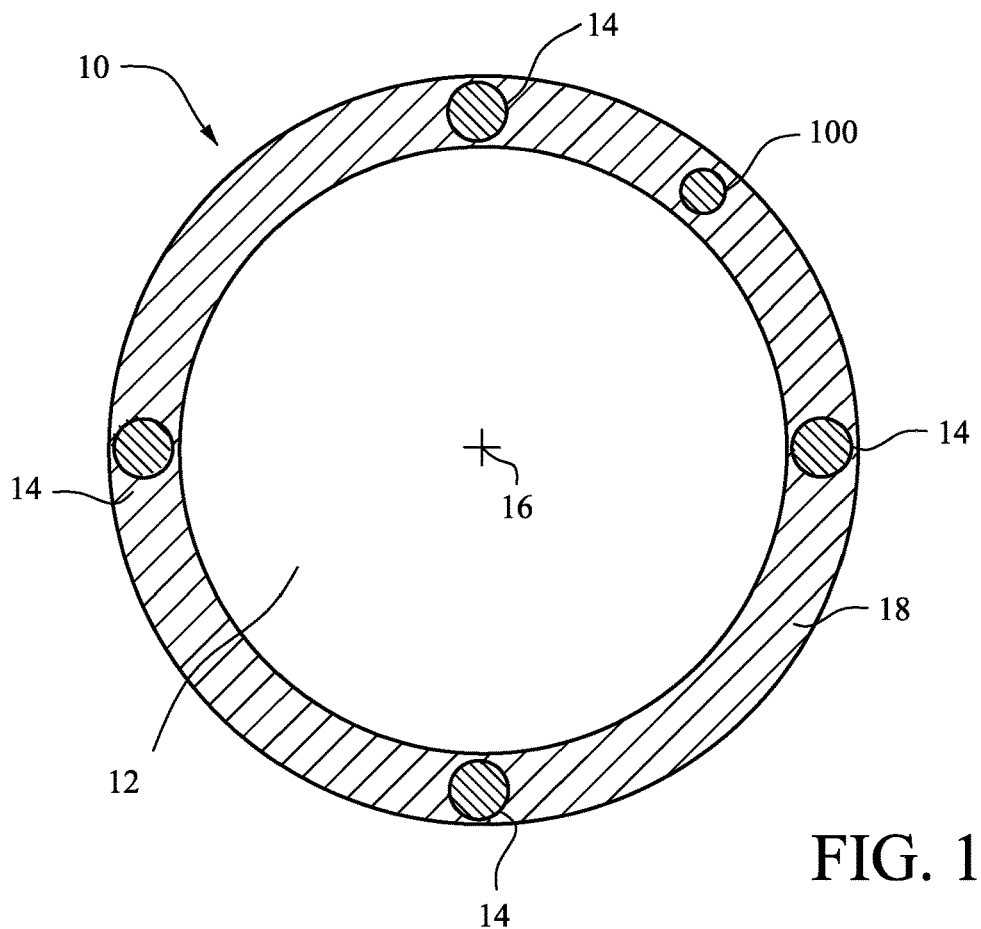
FIG. 1 is a cross-section through a diameter of a catheter where a central channel is open and wires for manipulating the catheter are illustrated.

FIG. 1 illustrates a cross-section of a catheter 10 (an example of a flexible tool) with a channel 12 (or lumen) and four wires 14 arrayed within a wall 18 of the catheter used to manipulate the shape of the catheter 10. The channel 12 allows for passage of another tool, instrument or substance through the catheter 10 and the channel 12 typically will be coextensive with any portion of the catheter 10 that is flexible. The center 16 of the channel 12 is indicated. An optical fiber 100 used to sense a shape of the catheter 10 is illustrated in the wall 18.

The optical fiber 100 can be used to sense a shape of the catheter 10 and is embedded into the wall 18 and has a diameter (or cross-sectional area) that does not interfere with an instrument that is inserted into the channel 12. Preferably, the optical fiber 100 is coextensive with all portions of the catheter 10 where shape sensing is desired.

Figure 2:
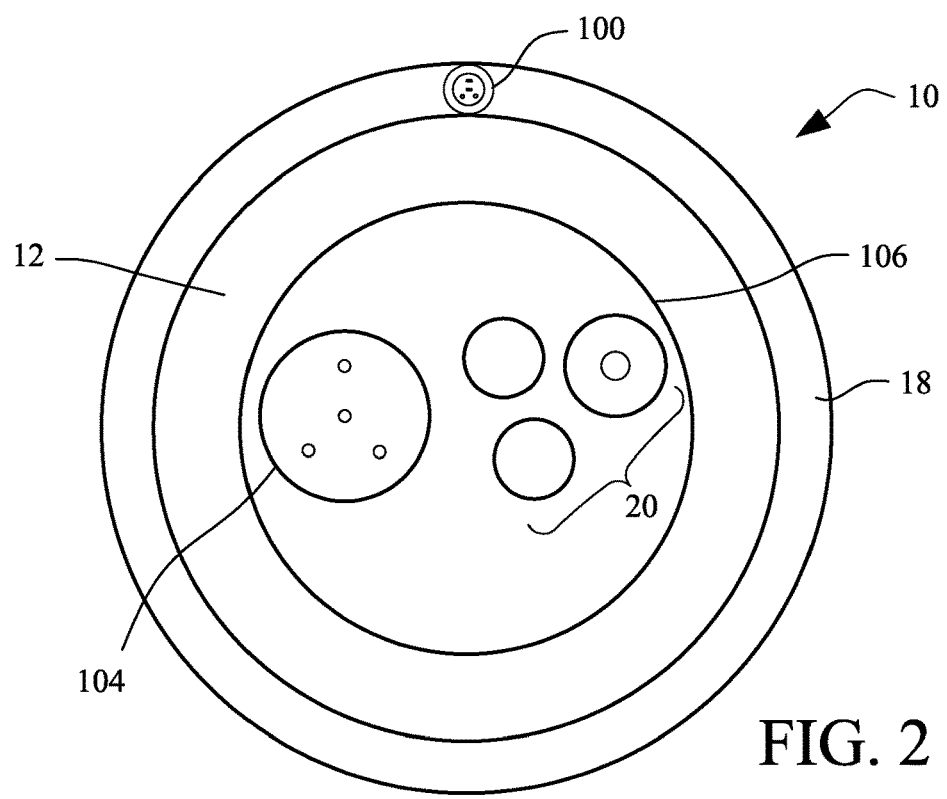
FIG. 2 is a cross-section through a diameter of a catheter where a central channel includes control wires for an instrument and an optical fiber.
Figure 3:
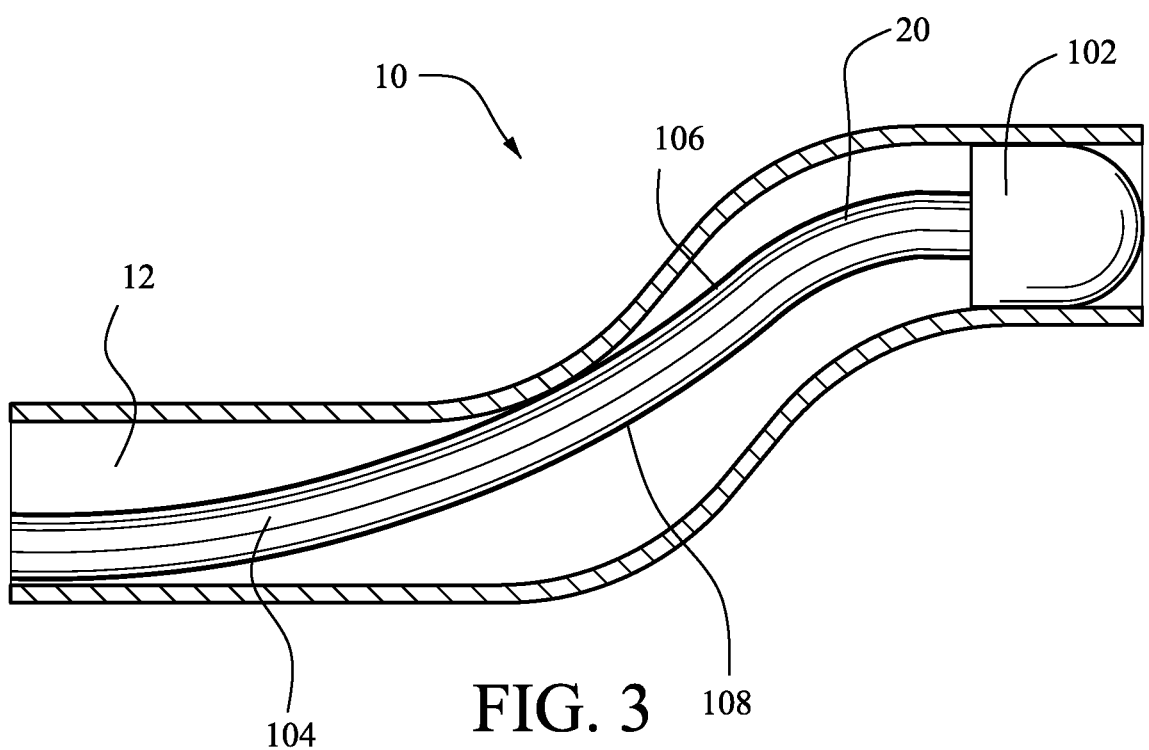
FIG. 3 is a cross-section through a longitudinal direction of a catheter where a central channel includes control wires and an optical fiber

FIGS. 2 and 3 illustrate the catheter 10 with an instrument 108 (illustrated as a probe including a probe flexible shaft 106 with an optical imaging device 102) with operational lines 20 extending through the probe flexible shaft 106. The operational lines 20 occupy less space within the width of the channel 12 than the optical imaging device 102, which, as illustrated, is sized to occupy substantially all of the diameter (or width) of the channel 12. In alternative examples the optical imaging device does not occupy a substantial diameter of the channel but occupies a diameter larger than the probe flexible shaft 106 and operational lines 20. This leaves usable space adjacent to the operational lines 20 within channel 12. In this example, the operational lines 20 can be provided in the probe flexible shaft 106 with a diameter sized to fit within the channel 12 without occupying the width of channel 12. The operational lines 20 can include control wires for navigating the instrument 108, optics for a camera, electrical wires, as well as lumens for suction/vacuum/delivery.

FIG. 3 illustrates a section of the catheter 10, the instrument 108 with operational lines 20 and optical imaging device 102, and a second optical fiber 104 (where the operational lines and optical fiber are not hatched for simplicity). The wires 14 are omitted for simplicity and the optical imaging device is only schematically illustrated. As is evident from this figure, the second optical fiber 104 can be (and is illustrated) significantly larger than the optical fiber 100 due to the size of the wall 18 versus the channel 12.

With the configuration illustrated in FIGS. 2 and 3, the second optical fiber 104 can be inserted into the catheter 10 simultaneously with the instrument 108. In one example, the second optical fiber 104 maybe attached to the optical imaging device 102 and extend through a lumen in the probe flexible shaft 106. In an alternative example, the second optical fiber is attached to the optical imaging device 102 but does not extend through the probe flexible shaft 106 but is alternatively free floating in the channel 12. Once the catheter 10 is in its desired location, the instrument 108 can be removed and replaced by another instrument. For example, a probe can be used during insertion of the catheter 10 and then removed and replaced by another instrument such as a biopsy tool (e.g. biopsy needle, scissors, graspers, cutting tools, etc.), an ablation tool (e.g. RF probe, ultrasound transducer, cryotherapy device, etc.), or imaging device (e.g. ultrasound, OCT, etc.). When the instrument 108 is removed, the second optical fiber 104 will also be removed. In one example the second optical fiber 104 is independent of the instrument 108 and so is removed independently. In another example the second optical fiber 104 is attached to instrument 108. The optical fiber 100 can be used to continually sense the shape of the catheter 10 and can be used to confirm that the shape of the catheter 10 does not change due to removal and replacement of instrument 108. This configuration illustrates an example of a repeatably removable optical fiber in that the second optical fiber 104 can be inserted and removed without changing (other than, perhaps, wear) the catheter 10, channel 12, second optical fiber 104, etc.

The second optical fiber 104 may be used for increased accuracy of measurement of the shape of the catheter 10 and/or location of the instrument 108. Accuracy may be analyzed with the following equation:

$$\frac{d\phi}{d\tau} = C * r^2 * \frac{d\theta}{d\ell},$$

where change in phase ($d\phi$) as a function of twist ($d\tau$) equals a constant (C) times the square of the radius of the peripheral core ($r^2$) times the spin rate of the fiber ($d\theta/dl$). The second optical fiber 104 may increase accuracy by way of a diameter that is larger than that of the optical fiber 100 because all other components of the equation will remain constant or substantially constant if the fiber diameter (or radius) is increased. At least within certain size ranges (e.g., diameter ranges) of optical fibers, shape change that results in twisting is a limiting factor for sensing shape. With a multi-core optical fiber, sensitivity to twist increases proportionally to the square of the radius of the peripheral cores, whereas bend sensitivity increases linearly. This occurs, at least in part, because a peripheral core (one that is not located on a central axis of the fiber) will also be stretched or compressed when the fiber undergoes a twisting motion due to the peripheral core being located away from the central axis. For example, the peripheral core may be arranged helically about the central axis and thus could be stretched or compressed based upon the direction of twist versus helix direction. Increasing diameter from 200 microns to 500 microns would theoretically result in accuracy increasing by a factor of 6.25, but in practice the increase in accuracy may be approximated as a factor of 5.

By inserting a larger fiber (e.g., second optical fiber 104) while the catheter 10 is being guided into position, increased accuracy can be achieved while taking advantage of unused space behind whatever instrument 108 (e.g., an optical imaging device) is being used. Then, when the instrument 108 is removed, space previously used by the second optical fiber 104 can be utilized by a larger instrument while the optical fiber 100 is used to continually measure the shape of the catheter 10 because continual measurement of the shape may require less accurate measurements and/or a more accurate measurement technique may be used once the initial shape is determined.

In some implementations, the larger fiber (e.g., second optical fiber 104) is also used to increase the accuracy when the larger fiber is not used to provide shape measurements. For example, in these implementations, when only a smaller fiber (e.g., the optical fiber 100) is used in measuring of the shape of the catheter 10, one or more previous measurements provided by the larger fiber is used to augment the readings from the smaller fiber. Some implementations determine a correction for the smaller optical fiber using one or more previous measurements provided by the larger fiber. Such a correction may be determined through any appropriate manner, and comprise a single value or a set of values for different shape-related parameters. Such a correction may be constant or vary with environmental factors or the physical configuration of the optical fiber. As one example, the correction may be calculated as a scaled or unscaled difference between the shape sensed with the larger optical fiber (by itself or with the smaller optical fiber), and the shape sensed without the larger optical fiber (e.g. with the smaller optical fiber only). The correction may indicate adjustments to one, some, or all of the shape-related parameters (e.g., physical parameters such as those involving yaw, pitch, strain, and/or twist), and be applied at some or all of the sensor locations along the fiber. In some embodiments, the sensed shape is used to derive the necessary phase readings, and the correction comprises adjustments to the phase readings used in shape sensing.

In embodiments where multiple data sets are taken with the larger optical fiber and the smaller optical fiber, the correction may be determined using more complex methods. For example, best fit estimates may be calculated as a function of the magnitude and/or direction of one or more of the measured yaw, pitch, strain, twist.

It should be noted that FIG. 3 illustrates the second optical fiber 104 unconstrained within the channel 12 and thus the shape of the second optical fiber 104 is not identical to the catheter 10. In this example, the second optical fiber is attached to the instrument 108 and thus a distal end of the second optical fiber is fixed relative to the instrument 108. This approach may be acceptable in some implementations. For example, this approach may be preferred in some implementations where only the location of the distal end of the instrument 108 and/or the location the distal end of the catheter 10 is important. If the shape over the length of the catheter 10 is important, then structure can be added proximal to the distal end of the instrument 108 such that the second optical fiber 104 is radially constrained to be substantially the same as the channel 12 (and thus the catheter 10) along any portion (i.e., the entire length or only part of the length) of the catheter 10 that is of interest to the user.

Also, the channel 12 is illustrated as a closed O-shape that is coextensive with the length of the catheter 10. However, the channel 12 could be any convenient shape, which could include an open profile or cross-section such as a U-shape. The channel 12 may be coextensive with the length of the catheter 10 or limited to part of the length.

The optical fiber 100 is illustrated as embedded in the wall 18, but the benefits of the second optical fiber 104 can be achieved if the optical fiber 100 is not embedded within the wall 18. For example, the optical fiber 100 could be attached to a surface of the wall 18 (e.g., the outer wall), which would allow the benefits described above. Alternatively, the optical fiber 100 can be contained within a lumen embedded into the wall 18, such that the optical fiber 100 is partially constrained within the lumen within the wall 18 but can have a limited amount of longitudinal, rotational and radial movement.

Although optical fibers with a diameter have been discussed throughout this disclosure, the present technology is not limited to optical fibers with a circular cross section. Thus diameter of the fiber is used herein to also encompass a major distance of the cross-section of fibers with a non-circular cross-section.

The optical fibers discussed throughout this disclosure may include single or multicore fibers. For example, the optical fiber 100 and the second optical fiber 104 may be either a single core fiber or a multicore fiber.

As described herein, an aspect of the present technology includes a method for sensing a shape of the flexible tool comprising: sensing the shape of the flexible tool using at least a second optical fiber after the second optical fiber has been inserted into a channel of the flexible tool; and sensing the shape of the flexible tool using the first optical fiber and not the second optical fiber after the second optical fiber has been removed from the channel. The second optical fiber includes a diameter larger than that of the first optical fiber.

In examples, the method further comprises: (a) performing an action with an operable element simultaneous to the sensing the shape of the flexible tool using the first optical fiber after the second optical fiber has been removed and the operable element has been inserted into the flexible tool; (b) determining that the second optical fiber has been inserted into the channel; (c) determining that the second optical fiber has been removed from the channel; and/or (d) sensing the shape of the flexible tool using only the first optical fiber.

The techniques described herein can be implemented using a control system. For example, any of the flexible tools described herein may also comprise a control system configured to operate with the optical fibers. The control system may be configured to sense the shape of the flexible tool using at least a second optical fiber after the second optical fiber has been inserted into the flexible portion, and to sense the shape of the flexible tool using a first optical fiber and not the second optical fiber after the second optical fiber has been removed from the flexible portion.

In various embodiments, the control system may include any one or combination of the following. The control system may be further configured to determine whether the second optical fiber is inserted into a flexible portion, lumen, channel, or other part of the flexible tool. The control system may be further configured to determine a correction for the first optical fiber based on a reading from the second optical fiber. The control system may be further configured to sense the shape of the flexible tool using the first optical fiber by using a reading from the first optical fiber and a correction (such as a correction determined based on a reading from the second optical fiber.)

In some embodiments, the control system includes at least one memory and at least one processor, and often a plurality of processors. The control system also includes programmed instructions (e.g., a computer-readable medium storing the instructions) to implement some or all of the methods described in accordance with aspects disclosed herein. The control system may include two or more data processing circuits with one portion of the processing optionally being performed on or adjacent the tool, and another portion of the processing being performed at a station (e.g. an operator input system or central processing system or the like) remote from the tool. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, the control system supports wireless communication protocols such as Bluetooth, IrDA, HomeRF, IEEE 802.11, DECT, and Wireless Telemetry.

While the present technology has been described in connection with several practical examples, it is to be understood that the technology is not to be limited to the disclosed examples, but on the contrary, is intended to cover various modifications and equivalent arrangements included within the spirit and scope of the technology.

The invention claimed is:

1. A system comprising:
a tool body with a flexible portion, a proximal end, and a distal end, the tool body defining a central channel in the flexible portion, the central channel having a longitudinal axis;
a first optical fiber within the flexible portion, the first optical fiber having a first diameter and being configured to sense a shape of the flexible portion; and
an instrument insertable into and removable from the central channel, the instrument comprising a shaft and an operable component at a distal end of the shaft, the operable component having a larger major dimension normal to the longitudinal axis than the shaft;
a second optical fiber insertable into and removable from the central channel within the flexible portion simultaneously with the instrument, the second optical fiber having a second diameter, the second diameter being larger than the first diameter, wherein the second optical fiber, when inserted into the central channel within the flexible portion, is configured to sense the shape of the flexible portion; and
a control system configured to:
when the second optical fiber is inserted into the flexible portion, sense the shape of the flexible portion using the first optical fiber and the second optical fiber and calculate a correction for the first optical fiber based on a difference between the shape sensed with the first optical fiber and the shape sensed with the second optical fiber, wherein the correction comprises an adjustment to a shape-related parameter or to a phase reading used in shape sensing with the first optical fiber; and
after the second optical fiber has been removed from the flexible portion, sense the shape of the flexible portion using the first optical fiber and not the second optical fiber, and determine the shape of the flexible portion using a phase reading from the first optical fiber and the correction.

2. The system according to claim 1, wherein the second optical fiber is attached to the operable component.

3. The system according to claim 1, wherein the operable component is an optical imaging device.

4. The system according to claim 2, wherein the second optical fiber extends through the shaft.

5. The system according to claim 2, wherein the second optical fiber does not extend through the shaft.

6. The system according to claim 1, wherein the first optical fiber is fixed to or within a wall of the tool body.

7. A method for sensing a shape of a flexible tool, the flexible tool having a first optical fiber configured to sense a shape of the flexible tool, the method comprising:
 sensing the shape of the flexible tool using the first optical fiber and a second optical fiber after the second optical fiber has been inserted into a central channel of the flexible tool, wherein the second optical fiber has a diameter larger than that of the first optical fiber;
 sensing the shape of the flexible tool using the first optical fiber and not the second optical fiber after the second optical fiber has been removed from the central channel;
 calculating, when a shape of the flexible tool is sensed with both the first optical fiber and the second optical fiber, a correction for the first optical fiber based on a difference between the shape sensed with the first optical fiber and the shape sensed with the second optical fiber, wherein the correction comprises an adjustment to a shape-related parameter or to a phase reading used in shape sensing with the first optical fiber; and
after the second optical fiber has been removed from the central channel, determining the shape of the flexible tool using a phase reading from the first optical fiber and the correction.

8. The method of claim 7, further comprising:
performing an action with an operable element simultaneous to the sensing the shape of the flexible tool using the first optical fiber after the second optical fiber has been removed and the operable element has been inserted into the central channel of the flexible tool.

9. The method of claim 7, further comprising:
re-sensing the shape of the flexible tool using at least the second optical fiber after a shape of the flexible tool has changed.

10. The method of claim 7, further comprising:
determining that the second optical fiber has been inserted into the central channel, and
determining that the second optical fiber has been removed from the central channel.

* * * * *